(12) United States Patent
Perkins et al.

(10) Patent No.: US 8,328,835 B2
(45) Date of Patent: Dec. 11, 2012

(54) SYSTEM FOR OPERATING AND CONTROLLING A PNEUMATICALLY DRIVEN VITRECTOMY PROBE

(75) Inventors: James T. Perkins, St. Charles, MO (US); Brian D. McCary, St. Louis, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 546 days.

(21) Appl. No.: 12/329,872

(22) Filed: Dec. 8, 2008

(65) Prior Publication Data

US 2010/0145374 A1 Jun. 10, 2010

(51) Int. Cl.
*A61B 17/32* (2006.01)
(52) U.S. Cl. ...................................................... 606/170
(58) Field of Classification Search .................. 606/170, 606/115, 162, 168, 173, 1, 107, 166, 171, 606/176, 177; 173/90, 200, 206; 83/639.1, 83/639.2, 639.5, 639.7
See application file for complete search history.

(56) References Cited

U.S. PATENT DOCUMENTS

| | | | | |
|---|---|---|---|---|
| 4,030,391 A | * | 6/1977 | Swanson et al. | 83/137 |
| 4,388,776 A | * | 6/1983 | Spring | 446/197 |
| 4,577,629 A | * | 3/1986 | Martinez | 606/171 |
| 6,547,749 B2 | * | 4/2003 | Hansen | 601/48 |
| 6,938,704 B2 | * | 9/2005 | Berger et al. | 173/201 |
| 2004/0049217 A1 | | 3/2004 | Ross | |
| 2008/0172078 A1 | | 7/2008 | Svetic | |

FOREIGN PATENT DOCUMENTS

| | | |
|---|---|---|
| EP | 1 199 053 A1 | 4/2002 |
| WO | WO 01/30281 A1 | 5/2001 |

OTHER PUBLICATIONS

International Search Report (PCTISA/210) and Written Opinion (PCT/ISA/1237) mailed on Mar. 25, 2010.

* cited by examiner

*Primary Examiner* — Ryan Severson
*Assistant Examiner* — Anh Dang
(74) *Attorney, Agent, or Firm* — Jeffrey B. Powers

(57) ABSTRACT

A pneumatically driven vitrectomy probe system includes a movable member disposed within a cylinder to define an enclosed pressure chamber, which has an inlet and an outlet. A pressure transducer senses the pressure level within the enclosed pressure chamber, and a valve communicates pressurized air to the inlet of the enclosed pressure chamber based on the pressure level. A displacement device coupled to the movable member extends and retracts the movable member within the enclosed pressure chamber, to respectively increase and decrease the pressure level of pressurized air communicated via the chamber outlet. The pressurized air is communicated to enclosed volume within a pneumatically activated vitrectomy probe, which includes a hollow inner cutting member disposed within the hollow outer member. Upon extension of the displacement member, the resulting increase in pressure level of the pressurized air in the enclosed volume acts against the biasing spring to move the hollow inner cutting member, to cut vitreous material extending within the hollow outer member.

18 Claims, 3 Drawing Sheets

SYSTEM FOR OPERATING AND CONTROLLING A PNEUMATICALLY DRIVEN VITRECTOMY PROBE

FIELD

The present invention relates to ophthalmic microsurgical probes such as vitrectomy probes, and control of such as vitrectomy probes.

BACKGROUND

This section provides background information related to the present disclosure which is not necessarily prior art.

Ophthalmic surgical procedures on the posterior segment of the eye generally require the cutting and/or removal of vitreous humor, a transparent jelly-like material that fills the posterior segment of the eye. The vitreous humor, or vitreous, is composed of numerous microscopic transparent fibers that are often attached to the retina. Therefore, cutting and removal of the vitreous must be done with great care to avoid traction on the retina (i.e., the separation of the retina from the choroid), a retinal tear, or cutting and removal of the retina itself.

The use of microsurgical cutting probes in posterior segment ophthalmic surgery is well known. Such vitrectomy probes are typically inserted through an incision in the sclera near the pars plana. The surgeon may also insert other microsurgical instruments such as a fiber optic illuminator, an infusion cannula, or an aspiration probe during the posterior segment surgery. The surgeon may perform the surgical procedure while viewing the eye under a microscope.

Conventional vitrectomy probes typically include a hollow inner cutting member coaxially disposed within a hollow outer cutting member through which vitreous humor is aspirated. Both the inner and outer cutting members cooperate to cut the vitreous, and the cut vitreous is then aspirated away through the inner cutting member.

SUMMARY

This section provides a general summary of the disclosure, and is not a comprehensive disclosure of its full scope or all of its features. The present disclosure relates to systems for operating and controlling a pneumatically driven vitrectomy probe. According to one aspect of the present disclosure, a pneumatically driven vitrectomy probe system is provided that includes a movable member disposed within a cylinder to define an enclosed pressure chamber, which has an inlet and an outlet therein. A pressure transducer senses the pressure level within the enclosed pressure chamber, and a valve communicates pressurized air to the inlet of the enclosed pressure chamber based on the sensed pressure level. A displacement device coupled to the movable member extends and retracts the movable member within the enclosed pressure chamber, to respectively increase and decrease the pressure level of pressurized air communicated via the chamber outlet. The pressurized air is communicated to enclosed volume within a pneumatically activated vitrectomy probe, which includes a hollow inner cutting member disposed within the hollow outer member. Upon extension of the displacement member, the resulting increase in pressure level of the pressurized air in the enclosed volume acts against the biasing spring to move the hollow inner cutting member, to thereby cut vitreous material extending with in the hollow outer member.

According to another aspect of the present disclosure, the movable member may comprise a piston or movable diaphragm disposed within the cylinder. The displacement device may comprise a drive motor coupled to a crank shaft that is connected to the movable member in a manner such that for every rotation of the motor the movable member is extended and retracted within the enclosed pressure chamber. The displacement device may alternatively comprise a drive solenoid coupled to the moveable member, for extending the moveable member within the enclosed pressure chamber when the solenoid is electrically activated and retracting the moveable member when the solenoid is deactivated. The drive mechanism respectively increases and decreases the pressure within the enclosed pressure chamber and the enclosed volume in the pneumatically operated vitrectomy probe.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
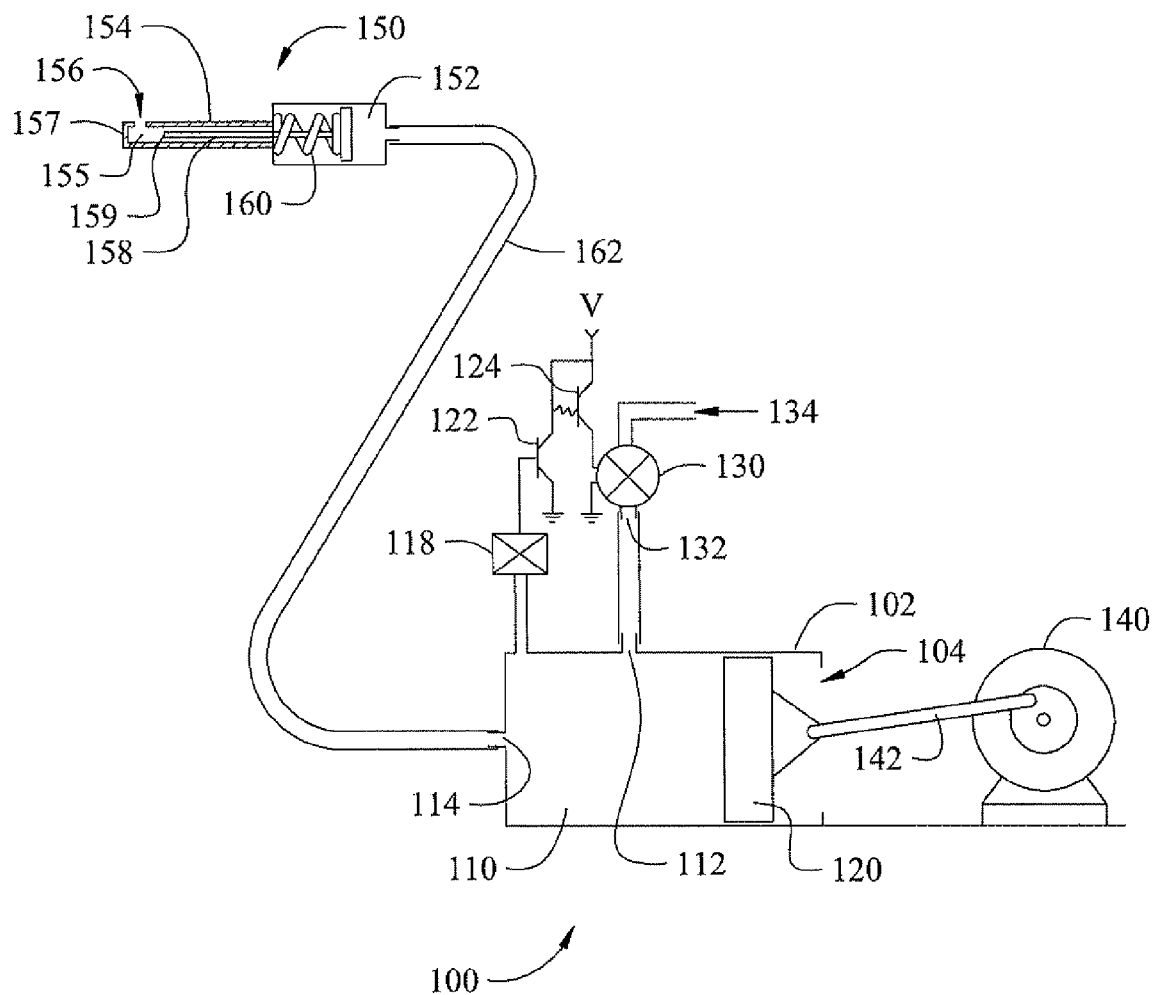
FIG. 1 shows a cross-sectional view of one embodiment of a system for a pneumatically driven vitrectomy probe, in accordance with the principles of the present disclosure.

Example embodiments will now be described more fully with reference to the accompanying drawings. The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

In the various embodiments, a control system for a pneumatically driven vitrectomy probe is provided. The control system generally comprises a cylinder having an open end in which a movable member is disposed, so as to define an enclosed pressure chamber. The enclosed pressure chamber within the cylinder also has an inlet and an outlet therein. A pressure transducer is in communication with the enclosed pressure chamber, for sensing the pressure level within the chamber. The outlet of a valve communicates pressurized air from a pressurized air source to the inlet of the enclosed pressure chamber based on the sensed pressure level.

The control system for a pneumatically driven vitrectomy probe further includes a displacement device coupled to the movable member so as to extend and retract the movable member within the enclosed pressure chamber, to respectively increase and decrease the pressure level and the pressurized air communicated via the chamber outlet. The pressurized air at the chamber outlet is in communication with an enclosed volume within a pneumatically activated vitrectomy probe. The pneumatically activated vitrectomy probe further includes a hollow outer member having a port near its distal end, and a hollow inner cutting member within the hollow outer member, which is biased by a spring away from the port. Upon extension of the displacement member, the resulting increase in pressure within the enclosed pressure chamber and the enclosed volume acts against the biasing spring to move the hollow inner cutting member towards the port. The hollow inner cutting member thereby cuts vitreous material that is extending through the port in the hollow outer member.

The movable member may comprise a piston or movable diaphragm disposed within the cylinder. The displacement device may comprise a drive motor coupled to a crank shaft that is connected to the movable member in a manner such that for every rotation of the motor the movable member is extended and retracted within the enclosed pressure chamber. The displacement device may alternatively comprise a drive solenoid coupled to the moveable member, for extending the moveable member within the enclosed pressure chamber when the solenoid is electrically activated and retracting the moveable member when the solenoid is deactivated. Accordingly, the drive mechanism respectively increases and decreases the pressure within the enclosed pressure chamber and the enclosed volume in the pneumatically operated vitrectomy probe. Unlike current vitrectomy probes utilizing pneumatic solenoids that rely on pressurized air to close the cutter, and then open the cutting using a pressure exhaust cycle to expel the pressurized air into the atmosphere, the following disclosed embodiments are much more quiet since they do not use a pneumatic solenoid.

Referring to FIG. 1, a first embodiment of a control system 100 for a pneumatically driven vitrectomy probe is shown. The pneumatically driven vitrectomy probe system 100 includes a cylinder 102 having an open end 104 in which a movable member or piston 120 is disposed, so as to define an enclosed pressure chamber 110. The enclosed pressure chamber 110 in cylinder 102 has an inlet 112 for receiving pressurized air, and an outlet 114 for communicating pressurized air to the pneumatically actuated vitrectomy probe. A pressure transducer 118 is in communication with the enclosed pressure chamber 110, for sensing the pressure level within the enclosed pressure chamber 110. A valve 130 is provided that has an outlet 132 in communication with the inlet 112 to the enclosed pressure chamber 110. The valve 130 communicates pressurized air from a pressurized air source 134 to the inlet 112 of enclosed pressure chamber 110 based on the pressure level sensed by the pressure transducer 118. This may be achieved by a pressure transducer 118 that produces a voltage level corresponding to the pressure level applied to the transducer. When the chamber is at the desired pressure level, the transducer 118 outputs a voltage to a circuit that gates a switch 122 (such as a triac) for switching a voltage V to ground. When the chamber pressure falls below the desired pressure level, the correspondingly reduced transducer voltage is insufficient to gate the switch 122, such that the voltage V gates a switch 124 to activate the valve 130, to thereby supply pressurized air to the inlet 112 of the pressure chamber 110. Preferably, the valve 130 communicates pressurized air from a pressurized air source 134 to the inlet 112 of enclosed pressure chamber 110 to maintain a desired pressure level.

The pneumatically driven vitrectomy probe system 100 includes a drive motor 140 coupled to a displacement device or crank shaft 142 that is connected to the piston 120 in a manner such that for every rotation of the motor 140, the piston 120 is extended and retracted within the enclosed pressure chamber 110. The extension and retraction thereby respectively increases and decreases the pressure level of the enclosed pressure chamber 110 and the pressurized air communicated via the outlet 112 of chamber 110. The continuous displacement and retraction of the piston 120 causes a pneumatically activated vitrectomy probe 150 to move a cutting member back and forth in a reciprocating manner.

The system 100 further includes a pneumatically activated vitrectomy probe 150 having an enclosed volume 152 that is in communication with the outlet 114 of the enclosed pressure chamber 110. The pneumatically activated vitrectomy probe 150 further includes a hollow outer member 154 having a port 156 near its distal end, and a hollow inner cutting member 158 within the hollow outer member 154. The hollow inner cutting member 158 is biased by a spring 160 away from the port 156. Upon extension of the piston 120, the resulting increase in pressure level within the probe's enclosed volume 152 acts against the biasing spring 160 to move the hollow inner cutting member 158 towards the port 156. In operation, the valve 130 communicates pressurized air to the pressure chamber 110 to maintain a desired pressure level that, upon extension of the piston 120, will cause the hollow inner cutting member 158 to move against the biasing spring 160 to a position in which the hollow inner cutting member 158 closes off the port 156. The end of the hollow inner cutting member 158 thereby cuts vitreous material extending through the port 156 in the hollow outer member 154.

The pneumatically driven vitrectomy probe is preferably an end-cutting vitrectomy probe 150 that comprises a hollow outer member or sleeve 154 having an inner bore 155 extending to a distal end portion of the sleeve 154. The hollow outer member or sleeve 154 has an opening or port 156 in the side of the distal end portion of the hollow sleeve 154, and a closed distal end 157. The end-cutting vitrectomy probe 150 further includes a hollow inner cutting member 158 within the hollow sleeve 154, which has a distal end defining a circumferential cutting edge 159. Accordingly, the hollow outer member 154 comprises a hollow sleeve having an opening port 156 in the side of the hollow sleeve at its distal end portion, with a hollow inner cutting member 158 having a distal end defining a cutting edge 159 slidably disposed within the hollow sleeve. The hollow inner cutting member 158 is movable towards the distal end of the hollow sleeve 154, such that the cutting edge 159 cuts any vitreous tissue disposed between the cutting edge 159 and the port 156. Specifically, the hollow inner cutting member 158 moves towards the distal end 157 of the sleeve 154, such that the circumferential cutting edge 159 slides adjacent to and closes off the port 156, to thereby cut any vitreous tissue disposed between the circumferential cutting edge 159 and the port 156. Increasing and decreasing the pressure level in the enclosed volume 152 causes the hollow inner cutting member 158 to move within the hollow sleeve 154 in a reciprocating manner, such that the cutting member 158 oscillates between a position of engagement with the port 156 and a position spaced apart from the port 156.

The drive motor 140 extends and retracts the piston 120 to increase and decrease the pressure, and cause the hollow inner cutting member 158 to be slidably displaced within the hollow sleeve 154 in a reciprocating manner. The hollow inner cutting member 158 oscillates between a cutting position where the hollow inner cutting member 158 closes off the opening port 156, and a retracted position where the hollow inner cutting member 158 is spaced apart from the opening port 156. Accordingly, the drive motor 140 thereby provides for repetitive cutting action of the hollow inner cutting member 158.

The drive motor 140 also operates in a continuous manner and generates a steady low-level noise, without generating any loud audible noise specifically attributed to either the action of extending the piston 120 or the action of retracting the piston 120. The end cutting vitrectomy probe may further include a pneumatic device (not shown) configured to apply a vacuum to the interior of the hollow outer member 154, for aspirating vitreous tissues through the opening port 156 and into the hollow outer sleeve 154, such as is well known in the art. This introduces portions of the vitreous tissues into the sleeve 154, which tissues may be cut and drawn through the interior of the hollow inner cutting member 158.

Figure 2:
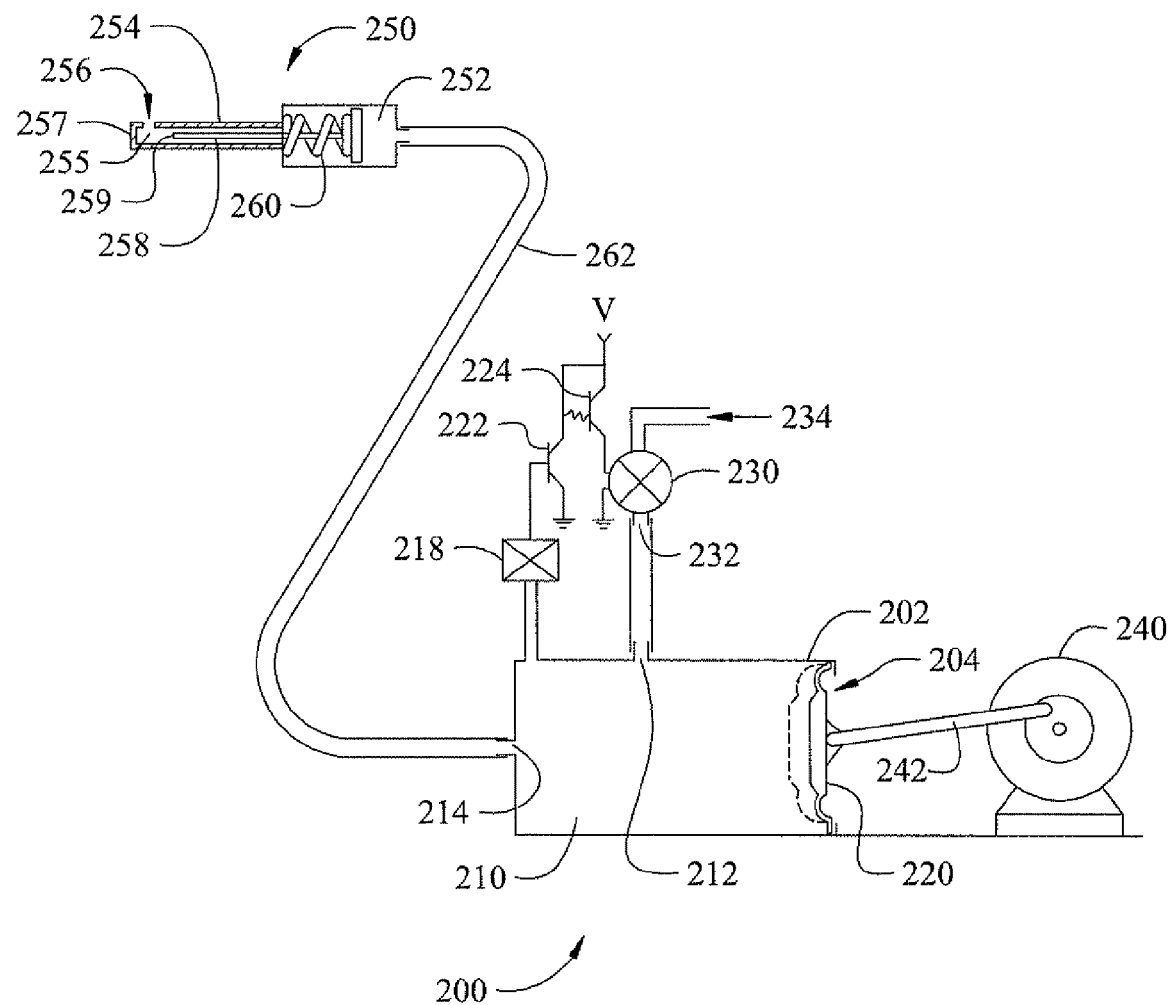
FIG. 2 shows a cross-sectional view of a second embodiment of a system for a pneumatically driven vitrectomy probe, in accordance with the principles of the present disclosure.

Referring to FIG. 2, a second embodiment of a control system 200 for a pneumatically driven vitrectomy probe is shown. The pneumatically driven vitrectomy probe system 200 includes a cylinder 202 having an open end 204 in which a movable diaphragm 220 is disposed, so as to define an enclosed pressure chamber 210. The enclosed pressure chamber 210 in cylinder 202 has an inlet 212 for receiving pressurized air, and an outlet 214 for communicating pressurized air to the pneumatically actuated vitrectomy probe. A pressure transducer 218 is in communication with the enclosed pressure chamber 210, for sensing the pressure level within the enclosed pressure chamber 210. A valve 230 is provided that has an outlet 232 in communication with the inlet 212 to the enclosed pressure chamber 210. The valve 230 communicates pressurized air from a pressurized air source 234 to the inlet 212 of enclosed pressure chamber 210 based on the pressure level sensed by the pressure transducer 218. This may be achieve by a transducer 218 that produces a voltage level corresponding to the pressure level applied to the transducer. When the chamber is at the desired pressure level, the transducer 218 outputs a voltage to a circuit that gates a switch 222 (such as a triac) for switching a voltage V to ground. When the chamber pressure falls below the desired pressure level, the correspondingly reduced transducer voltage is insufficient to gate the switch 222, such that the voltage V gates a switch 224 to activate the valve 230, to thereby supply pressurized air to the inlet 212 of the pressure chamber 210. Preferably, the valve 230 communicates pressurized air from a pressurized air source 234 to the inlet 212 of the enclosed pressure chamber 210 to maintain a desired pressure level.

The second embodiment of a pneumatically driven vitrectomy probe system 200 includes a drive motor 240 coupled to a crank shaft 242. The crank shaft 242 is connected to the movable diaphragm 220 in a manner such that for every rotation of the motor 240, the movable diaphragm 220 is extended and retracted within the enclosed pressure chamber 210. The extension and retraction thereby respectively increases and decreases the pressure level of the enclosed pressure chamber 210 and the pressurized air communicated via the outlet 214 of chamber 210. The continuous displacement and retraction of the movable diaphragm 220 causes a pneumatically activated vitrectomy probe 250 to move a cutting member back and forth in a reciprocating manner.

The system 200 further includes a pneumatically activated vitrectomy probe 250 having an enclosed volume 252 that is in communication with the outlet 214 of the enclosed pressure chamber 210. The pneumatically activated vitrectomy probe 250 further includes a hollow outer member 254 having a port 256 near its distal end, and a hollow inner cutting member 258 within the hollow outer member 254. The hollow inner cutting member 258 is biased by a spring 260 away from the port 256. Upon extension of the movable diaphragm 220, the resulting increase in pressure level within the probe's enclosed volume 252 acts against the biasing spring 260 to move the hollow inner cutting member 258 towards the port 256. In operation, the valve 230 communicates pressurized air to the pressure chamber 210 to maintain a desired pressure level that, upon extension of the movable diaphragm 220, will cause the hollow inner cutting member 258 to move against the biasing spring 260 to a position in which the hollow inner cutting member 258 closes off the port 256. The end of the hollow inner cutting member 258 thereby cuts vitreous material extending through the port 256 in the hollow outer member 254.

The pneumatically driven vitrectomy probe is preferably an end-cutting vitrectomy probe 250 that comprises a hollow outer member or sleeve 254 having an inner bore 255 extending to a distal end portion of the sleeve 254. The hollow outer member or sleeve 254 has an opening or port 256 in the side of the distal end portion of the hollow sleeve 254, and a closed distal end 257. The end-cutting vitrectomy probe 250 further includes a hollow inner cutting member 258 within the hollow sleeve 254, which has a distal end defining a circumferential cutting edge 259. Accordingly, the hollow outer member 254 comprises a hollow sleeve having an opening port 256 in the side of the hollow sleeve at its distal end portion, with a hollow inner cutting member 258 having a distal end defining a cutting edge 259 slidably disposed within the hollow sleeve. The hollow inner cutting member 258 is movable towards the distal end of the hollow sleeve 254, such that the cutting edge 259 cuts any vitreous tissue disposed between the cutting edge 259 and the opening port 256. Specifically, the hollow inner cutting member 258 moves towards the distal end 257 of the sleeve 254, such that the circumferential cutting edge 259 slides adjacent to and closes off the port 256, to thereby cut any vitreous tissue disposed between the circumferential cutting edge 259 and the port 256. Increasing and decreasing the pressure level in the enclosed volume 252 causes the hollow inner cutting member 258 to move within the hollow sleeve 254 in a reciprocating manner, such that the cutting member 258 oscillates between a position of engagement with the port 256 and a position spaced apart from the port 256.

The drive motor 240 extends and retracts the movable diaphragm 220 to increase and decrease the pressure, and cause the hollow inner cutting member 258 to be slidably displaced within the hollow sleeve 254 in a reciprocating manner. The hollow inner cutting member 258 oscillates between a cutting position where the hollow inner cutting member 258 closes off the opening port 256, and a retracted position where the hollow inner cutting member 258 is spaced apart from the opening port 256. Accordingly, the drive motor 240 thereby provides for repetitive cutting action of the hollow inner cutting member 258.

The drive motor 240 also operates in a continuous manner and generates a steady low-level noise, without generating any loud audible noise specifically attributed to either the action of extending the movable diaphragm 220 or the action of retracting the movable diaphragm 220. The end cutting vitrectomy probe may further include a pneumatic device (not shown) configured to apply a vacuum to the interior of the hollow outer member 254, for aspirating vitreous tissues through the opening port 256 and into the hollow outer sleeve 254. This introduces portions of the vitreous tissues into the sleeve 254, which tissues may be cut and drawn through the interior of the hollow inner cutting member 258.

Figure 3:
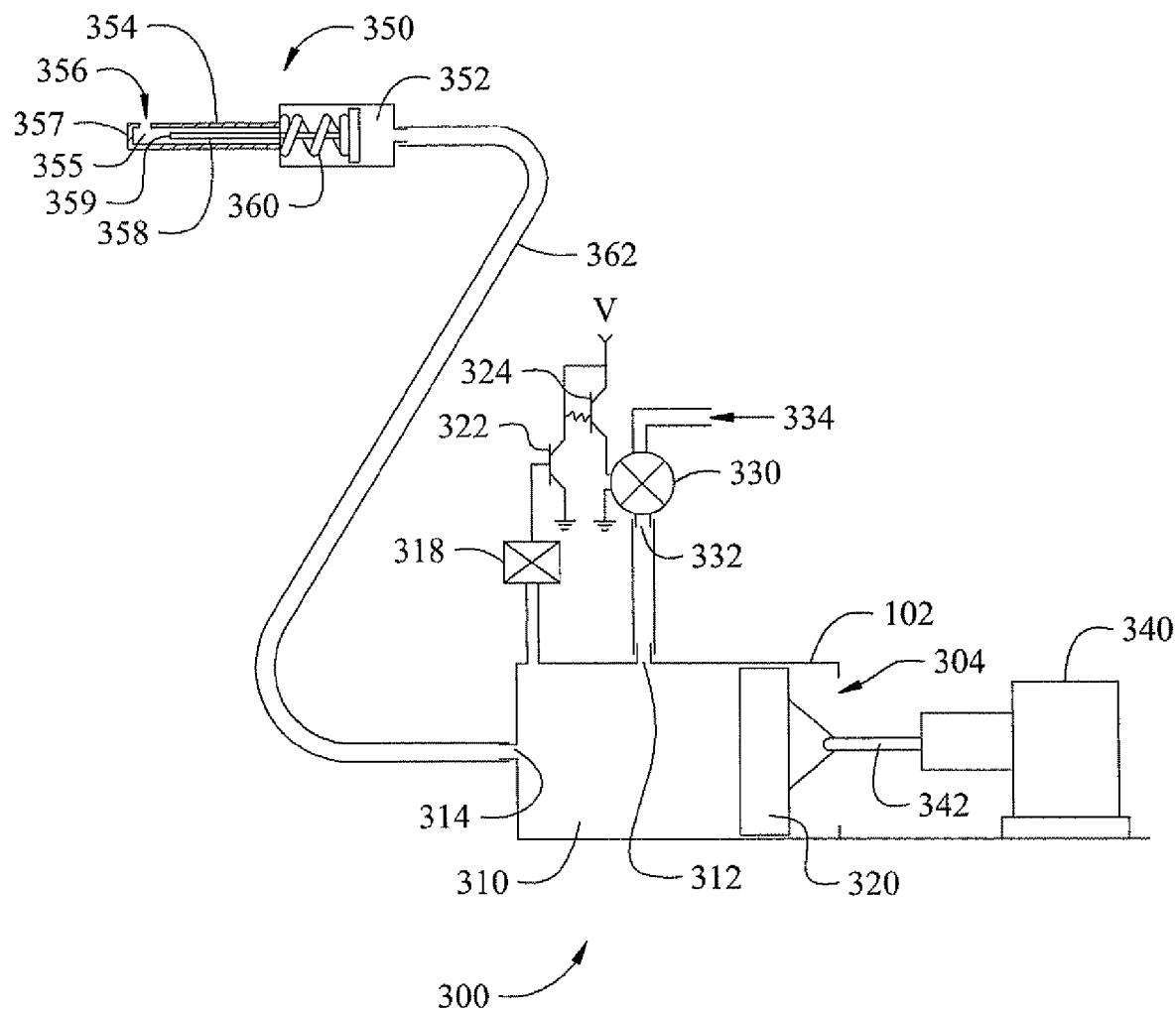
FIG. 3 shows a cross-sectional view of a third embodiment of a system for a pneumatically driven vitrectomy probe, in accordance with the principles of the present disclosure.

Referring to FIG. 3, a third embodiment of a control system 300 for a pneumatically driven vitrectomy probe is shown. The pneumatically driven vitrectomy probe system 300 includes a cylinder 302 having an open end 304 in which a piston 320 is disposed, so as to define an enclosed pressure chamber 310. The enclosed pressure chamber 310 in cylinder 302 has an inlet 312 for receiving pressurized air, and an outlet 314 for communicating pressurized air to the pneumatically actuated vitrectomy probe. A pressure transducer 318 is in communication with the enclosed pressure chamber 310, for sensing the pressure level within the enclosed pressure chamber 310. A valve 330 is provided that has an outlet 332 in communication with the inlet 312 to the enclosed pressure chamber 310. The valve 330 communicates pressurized air from a pressurized air source 334 to the inlet 312 of enclosed pressure chamber 310 based on the pressure level sensed by the pressure transducer 318. This may be achieved by a pressure transducer 318 that produces a voltage level corresponding to the pressure level applied to the transducer. When the chamber is at the desired pressure level, the transducer 318 outputs a voltage to a circuit that gates a switch 322 (such as a triac) for switching a voltage V to ground. When the chamber pressure falls below the desired pressure level, the correspondingly reduced transducer voltage is insufficient to gate the switch 322, such that the voltage V gates a switch 324 to activate the valve 330, to thereby supply pressurized air to the inlet 312 of the pressure chamber 310. Preferably, the valve 330 communicates pressurized air from a pressurized air source 334 to the inlet 312 of the enclosed pressure chamber 310 to maintain a desired pressure level.

The pneumatically driven vitrectomy probe system 300 includes a drive mechanism 340 coupled to a shaft 342 that is connected to the piston 320. The drive mechanism 340 may be a solenoid, for example, which extends the piston 320 when the solenoid is electrically activated, and retracts the piston 320 when the solenoid is deactivated. The shaft 342 is connected to the piston 320 in a manner such that activation and deactivation of the drive mechanism 340 causes the piston 320 to be extended and retracted within the enclosed pressure chamber 310. The extension and retraction thereby respectively increases and decreases the pressure level of the enclosed pressure chamber 310 and the pressurized air communicated via the outlet 312 of chamber 310. The continuous displacement and retraction of the piston 320 causes a pneumatically activated vitrectomy probe 350 to move a cutting member back and forth in a reciprocating manner.

The system 300 further includes a pneumatically activated vitrectomy probe 350 having an enclosed volume 352 that is in communication with the outlet 314 of the enclosed pressure chamber 310. The pneumatically activated vitrectomy probe 350 further includes a hollow outer member 354 having a port 356 near its distal end, and a hollow inner cutting member 358 within the hollow outer member 354. The hollow inner cutting member 358 is biased by a spring 360 away from the port 356. Upon extension of the piston 320, the resulting increase in pressure level within the probe's enclosed volume 352 acts against the biasing spring 360 to move the hollow inner cutting member 358 towards the port 356. In operation, the valve 330 communicates pressurized air to the pressure chamber 310 to maintain a desired pressure level that, upon extension of the piston 320, will cause the hollow inner cutting member 358 to move against the biasing spring 360 to a position in which the hollow inner cutting member 358 closes off the port 356. The end of the hollow inner cutting member 358 thereby cuts vitreous material extending through the port 356 in the hollow outer member 354.

The pneumatically driven vitrectomy probe is preferably an end-cutting vitrectomy probe 350 that comprises a hollow outer member or sleeve 354 having an inner bore 355 extending to a distal end portion of the sleeve 354. The hollow outer member or sleeve 354 has an opening or port 356 in the side of the distal end portion of the hollow sleeve 354, and a closed distal end 357. The end-cutting vitrectomy probe 350 further includes a hollow inner cutting member 158 within the hollow sleeve 154, which has a distal end defining a circumferential cutting edge 359. Accordingly, the hollow outer member 354 comprises a hollow sleeve having an opening port 356 in the side of the hollow sleeve at its distal end portion, with a hollow inner cutting member 358 having a distal end defining a cutting edge 359 slidably disposed within the hollow sleeve. The hollow inner cutting member 358 is movable towards the distal end of the hollow sleeve 354, such that the cutting edge 359 cuts any vitreous tissue disposed between the cutting edge 359 and the opening port 356. Specifically, the hollow inner cutting member 358 moves towards the distal end 357 of the sleeve 354, such that the circumferential cutting edge 359 slides adjacent to and closes off the port 356, to thereby cut any vitreous tissue disposed between the circumferential cutting edge 359 and the port 356. Increasing and decreasing the pressure level in the enclosed volume 352 causes the hollow inner cutting member 358 to move within the hollow sleeve 354 in a reciprocating manner, such that the cutting member 358 oscillates between a position of engagement with the port 356 and a position spaced apart from the port 356.

The drive mechanism 340 extends and retracts the piston 320 to increase and decrease the pressure, and cause the hollow inner cutting member 358 to be slidably displaced within the hollow sleeve 354 in a reciprocating manner. The hollow inner cutting member 358 oscillates between a cutting position where the hollow inner cutting member 358 closes off the opening port 356, and a retracted position where the hollow inner cutting member 358 is spaced apart from the opening port 356. Accordingly, the drive mechanism 340 thereby provides for repetitive cutting action of the hollow inner cutting member 358.

The drive mechanism 340 also operates in a continuous manner and generates a steady low-level noise, without generating any loud audible noise specifically attributed to either the action of extending the piston 320 or the action of retracting the piston 320. The end cutting vitrectomy probe may further include a pneumatic device (not shown) configured to apply a vacuum to the interior of the hollow outer member 354, for aspirating vitreous tissues through the opening port 356 and into the hollow outer sleeve 354. This introduces portions of the vitreous tissues into the sleeve 354, which tissues may be cut and drawn through the interior of the hollow inner cutting member 358.

It should be understood from the above embodiments that one aspect of such designs is to quietly, accurately and efficiently drive a pneumatic vitrectomy probe or cutter. The above designs can easily be driven at high speeds, and are only limited by the speed of the drive motor or mechanism. One important feature of the above embodiments is the closed volume of air between the cylinder or enclosed pressure chamber and the vitrectomy probe volume. This feature, when combined with the ability to control the pressure level within the pressure chamber to maintain an amount of pressurized air, enables the vitrectomy probe to operate effectively at all cut rates. The above designs not only provide an effective pressure cycle for cutting vitreous, but also generate a low pressure stroke to pull the cutter completely open to allow efficient aspiration of the vitreous. Since the above designs do not require air pressure to be exhausted into the environment, as with probes driven by pneumatic solenoid operators, the above designs are inherently more quiet, where the only noise generated is from the drive mechanism.

From the above, it may be appreciated that the present invention provides an improvement to aspiration fluid flow control, to thereby control the flow rate of fluid aspirated from a surgical site. The present invention is illustrated herein by example, and various modifications may be made by a person of ordinary skill in the art. It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A pneumatically driven vitrectomy probe system, comprising:
    a cylinder having an open end in which a movable member is disposed so as to define an enclosed pressure chamber, the enclosed pressure chamber having an inlet and an outlet therein;
    a pressure transducer in communication with the enclosed pressure chamber, for sensing the pressure level within the enclosed pressure chamber;
    a valve having an outlet that is in communication with the inlet of the enclosed pressure chamber, wherein the valve communicates pressurized air from a pressurized air source to the inlet of enclosed pressure chamber based on the sensed pressure level;
    a displacement device coupled to the movable member so as to extend and retract the movable member within the enclosed pressure chamber, to respectively increase and decrease the pressure level of the chamber and the pressurized air being communicated via the outlet of the enclosed pressure chamber; and
    a pneumatically activated vitrectomy probe having an enclosed volume that is in communication with the outlet of the enclosed pressure chamber, the pneumatically activated vitrectomy probe further including a hollow outer member having a port near its distal end, and a hollow inner cutting member within the hollow outer member, which is biased by a spring away from said port, whereupon extension of the displacement member, the resulting increase in pressure within the enclosed volume acts against the biasing spring to move the hollow inner cutting member towards the port, to thereby cut vitreous material extending through the port in the hollow outer member.

2. The pneumatically driven vitrectomy probe system of claim 1 wherein the valve communicates pressurized air from a pressurized air source to the inlet of enclosed pressure chamber to maintain a pressure level that upon extension of the displacement device will cause the hollow inner cutting member to move against the biasing spring to a position in which the hollow inner cutting member closes off the port.

3. The pneumatically driven vitrectomy probe system of claim 1 wherein the operation of the displacement device causes the hollow inner cutting member to move back and forth relative to the port in a reciprocating manner.

4. The pneumatically driven vitrectomy probe system of claim 1 wherein the hollow outer member comprises a hollow sleeve having an opening port in the side of the hollow sleeve at its distal end portion, and the hollow inner cutting member is slidably disposed within the hollow sleeve and has a distal end defining a cutting edge, the hollow inner cutting member being movable towards the distal end of the hollow sleeve such that the cutting edge cuts any vitreous tissue disposed between the cutting edge and the opening port.

5. The pneumatically driven vitrectomy probe system of claim 4, wherein the displacement device causes the hollow inner cutting member to be slidably displaced within the hollow sleeve in a reciprocating manner, such that the cutting member oscillates between a cutting position where the hollow inner cutting member closes off the opening port, and a position where the hollow inner cutting member is spaced apart from the opening port, to thereby provide for repetitive cutting action.

6. The pneumatically driven vitrectomy probe system of claim 1 wherein the movable member comprises a piston slidably disposed within the cylinder, and the displacement device comprises a crank shaft that is connected to the piston in a manner such that for every rotation of a drive motor the piston is extended and retracted within the enclosed pressure chamber, to thereby respectively increase and decrease the pressure within the enclosed pressure chamber and the enclosed volume in the pneumatically operated vitrectomy probe.

7. The pneumatically driven vitrectomy probe system of claim 1, wherein the movable member comprises a movable diaphragm disposed within the cylinder, and the displacement device comprises a crank shaft that is connected to the movable diaphragm in a manner such that for every rotation of a drive motor the movable diaphragm is extendably displaced into the enclosed pressure chamber in the cylinder and then retracted, to thereby respectively increase and decrease the pressure within the enclosed pressure chamber and the enclosed volume in the pneumatically operated vitrectomy probe.

8. The pneumatically driven vitrectomy probe system of claim 1 wherein the movable member comprises a piston slidably disposed within the cylinder, and the displacement device comprises a drive solenoid coupled to the piston, which extends the piston within the enclosed pressure chamber when the solenoid is electrically activated and retracts the piston when the solenoid is deactivated, to thereby respectively increase and decrease the pressure within the enclosed pressure chamber and the enclosed volume in the pneumatically operated vitrectomy probe.

9. A pneumatically driven vitrectomy probe system, comprising:
    a cylinder having an open end in which a piston is disposed so as to define an enclosed pressure chamber, the enclosed pressure chamber having an inlet for receiving pressurized air, and an outlet for communicating pressurized air to a pneumatically actuated vitrectomy probe;
    a pressure transducer in communication with the enclosed pressure chamber, for sensing a pressure level within the enclosed pressure chamber;
    a valve having an outlet that is in communication with the inlet to the enclosed pressure chamber, wherein the valve communicates pressurized air from a pressurized air source to the inlet of enclosed pressure chamber based on the pressure level;
    a drive motor coupled to a crank shaft that is connected to the piston in a manner such that for every rotation of the motor the piston is extended and retracted within the enclosed pressure chamber, to thereby respectively increase and decrease the pressure level of the chamber and the pressurized air communicated via the outlet of the enclosed pressure chamber; and a pneumatically activated vitrectomy probe having an enclosed volume that is in communication with the outlet of the enclosed pressure chamber, the pneumatically activated vitrectomy probe further including a hollow outer member having a port near its distal end, and a hollow inner cutting member within the hollow outer member, which is biased by a spring away from the port, whereupon extension of the piston, the resulting increase in pressure level within the enclosed volume acts against the biasing spring to move the hollow inner cutting member towards the port, to thereby cut vitreous material extending through the port in the hollow outer member.

10. The pneumatically driven vitrectomy probe system of claim 9 wherein the valve communicates pressurized air from a pressurized air source to the inlet of enclosed pressure chamber to maintain a pressure level that upon extension of the piston will cause the hollow inner cutting member to move against the biasing spring to a position in which the hollow inner cutting member closes off the port.

11. The pneumatically driven vitrectomy probe system of claim 9 wherein the continuous displacement and retraction of the piston causes the hollow inner cutting member to move back and forth relative to the port in a reciprocating manner.

12. The pneumatically driven vitrectomy probe system of claim 9 wherein the hollow outer member comprises a hollow sleeve having an opening port in the side of the hollow sleeve at its distal end portion, and the hollow inner cutting member is slidably disposed within the hollow sleeve and has a distal end defining a cutting edge, the hollow inner cutting member being movable towards the distal end of the hollow sleeve such that the cutting edge cuts any vitreous tissue disposed between the cutting edge and the opening port.

13. The pneumatically driven vitrectomy probe system of claim 12, wherein the extension and retraction of the piston causes the hollow inner cutting member to be slidably displaced within the hollow sleeve in a reciprocating manner, such that the cutting member oscillates between a cutting position where the hollow inner cutting member closes off the opening port, and a position where the hollow inner cutting member is spaced apart from the opening port, to thereby provide for repetitive cutting action.

14. A pneumatically driven vitrectomy probe system, comprising:
a cylinder having an open end in which a movable diaphragm is disposed so as to define an enclosed pressure chamber, the enclosed pressure chamber having an inlet for receiving pressurized air, and an outlet for communicating pressurized air to a pneumatically actuated vitrectomy probe;
a pressure transducer in communication with the enclosed pressure chamber, for sensing a pressure level within the enclosed pressure chamber;
a valve having an outlet that is in communication with the inlet to the enclosed pressure chamber, wherein the Valve communicates pressurized air from a pressurized air source to the inlet of the enclosed pressure chamber based on the pressure level;
a drive motor coupled to a crank shaft that is connected to the movable diaphragm in a manner such that for every rotation of the motor the movable diaphragm is extendably displaced into the enclosed pressure chamber in the cylinder and then retracted, to thereby respectively increase and decrease the pressure within the enclosed pressure chamber and the enclosed volume in the pneumatically operated vitrectomy probe; and
a pneumatically activated vitrectomy probe having an enclosed volume that is in communication with the outlet of the enclosed pressure chamber, the pneumatically activated vitrectomy probe further including a hollow outer member having a port near its distal end, and a hollow inner cutting member within the hollow outer member, which is biased by a spring away from the port, whereupon extension of the movable diaphragm, the resulting increase in pressure level within the enclosed volume acts against the biasing spring to move the hollow inner cutting member towards the port, to thereby cut vitreous material extending through the port in the hollow outer member.

15. The pneumatically driven vitrectomy probe system of claim 14 wherein the valve communicates pressurized air from a pressurized air source to the inlet of enclosed pressure chamber to maintain a pressure level that upon extension of the diaphragm will cause the hollow inner cutting member to move against the biasing spring to a position in which the hollow inner cutting member closes off the port.

16. The pneumatically driven vitrectomy probe system of claim 14 wherein the continuous displacement and retraction of the diaphragm causes the hollow inner cutting member to move back and forth relative to the port in a reciprocating manner.

17. The pneumatically driven vitrectomy probe system of claim 14 wherein the hollow outer member comprises a hollow sleeve having an opening port in the side of the hollow sleeve at its distal end portion, and the hollow inner cutting member is slidably disposed within the hollow sleeve and has a distal end defining a cutting edge, the hollow inner cutting member being movable towards the distal end of the hollow sleeve such that the cutting edge cuts any vitreous tissue disposed between the cutting edge and the opening port.

18. The pneumatically driven vitrectomy probe system of claim 14, wherein the extension and retraction of the movable diaphragm causes the hollow inner cutting member to be slidably displaced the within the hollow sleeve in a reciprocating manner, such that the cutting member oscillates between a cutting position where the hollow inner cutting member closes off the opening port, and a position where the hollow inner cutting member is spaced apart from the opening port, to thereby provide for repetitive cutting action.

* * * * *